United States Patent
Hazen et al.

(10) Patent No.: US 12,092,648 B2
(45) Date of Patent: Sep. 17, 2024

(54) DETECTION OF GLUCURONIDATED AND 3-BROMOTYROSINE

(71) Applicant: The Cleveland Clinic Foundation, Cleveland, OH (US)

(72) Inventors: Stanley L. Hazen, Pepper Pike, OH (US); Zeneng Wang, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 124 days.

(21) Appl. No.: 17/668,261

(22) Filed: Feb. 9, 2022

(65) Prior Publication Data

US 2022/0163540 A1 May 26, 2022

Related U.S. Application Data

(62) Division of application No. 16/281,811, filed on Feb. 21, 2019, now Pat. No. 11,249,091.

(60) Provisional application No. 62/633,693, filed on Feb. 22, 2018.

(51) Int. Cl.
  *G01N 33/53* (2006.01)
  *G01N 33/68* (2006.01)

(52) U.S. Cl.
  CPC ... *G01N 33/6893* (2013.01); *G01N 2800/122* (2013.01); *G01N 2800/52* (2013.01)

(58) Field of Classification Search
  None
  See application file for complete search history.

(56) References Cited

U.S. PATENT DOCUMENTS

| | | | |
|---|---|---|---|
| 5,352,803 | A | 10/1994 | Mattingly |
| 5,359,093 | A | 10/1994 | Adamczyk et al. |
| 5,496,925 | A | 3/1996 | Mattingly |
| 5,573,904 | A | 11/1996 | Mattingly |
| 5,593,896 | A | 1/1997 | Adamczyk et al. |
| 6,306,576 | B1 | 10/2001 | Hazen et al. |
| 6,939,716 | B2 | 9/2005 | Heinecke |
| 2013/0309695 | A1* | 11/2013 | Soussi Gounni .. G01N 33/6893 435/7.92 |
| 2018/0292399 | A1* | 10/2018 | Verma ................. C12N 5/0609 |

OTHER PUBLICATIONS

Butz et al., Household Smoking Behavior: Effects on Indoor Air Quality and Health of Urban Children with Asthma, Matern Child Health J, 2011, 15, pp. 460-468. (Year: 2011).*
Adamczyk et al., Chemiluminescent acridinium-9-carboxamide boronic acid probes: application to a homogeneous glycated hemoglobin assay. Bioorg Med Chem Lett. Mar. 1, 2006;16(5):1324-8.
Adamczyk et al., Intrinsic factor-mediated modulation of cyanocobalamin-N-sulfonyl-acridinium-9-carboxamide chemiluminescence. Bioorg Med Chem Lett. Aug. 2, 2004;14(15):3917-21.
Adamczyk et al., Regiodependent luminescence quenching of biotinylated N-sulfonyl-acridinium-9-carboxamides by avidin. Org Lett. Oct. 16, 2003;5(21):3779-82.
Cowan et al., Biomarker-based asthma phenotypes of corticosteroid response. J Allergy Clin Immunol. Apr. 2015;135(4) 877-883.e1.
Torzewski et al., Animal models of C-reactive protein. Mediators Inflamm. 2014;2014:683598.
Van Der Vekens et al., Human and equine cardiovascular endocrinology: beware to compare. Cardiovascular Endocrinology. 2013;2(4):67-76.
Wedes et al., Noninvasive markers of airway inflammation in asthma. Clin Transl Sci. Apr. 2009;2(2):112-7.
Wedes et al., Urinary bromotyrosine measures asthma control and predicts asthma exacerbations in children. J Pediatr., Aug. 2011;159(2):248-55.e1.

* cited by examiner

*Primary Examiner* — Gary Counts
(74) *Attorney, Agent, or Firm* — Jason R. Bond; Casimir Jones, S.C.

(57) ABSTRACT

The present invention provides methods, kits, and compositions for: i) detecting the level of 3-bromotyrosine in a sample that has been treated to liberate 3-bromotyrosine from 4-O-glucuronide-3-bromotyrosine, and/or ii) detecting the level of 4-O-glucuronide-3-bromotyrosine, and/or the combined level of both 4-O-glucuronide-3-bromotyrosine and 3-bromotyrosine, in a sample that has not been treated to liberate 3-bromotyrosine from 4-O-glucuronide-3-bromotyrosine. In certain embodiments, such detected levels are used to: i) identify the presence, severity, or risk of an eosinophilic disorder (e.g., asthma or a TH2-high eosinophilic disorder); ii) identify therapy effective for treating asthma or an eosinophilic disorder; or iii) identify patients suitable for treatment with therapeutic agents targeted to asthma or an eosinophilic disorder.

8 Claims, 15 Drawing Sheets

FIG. 4A
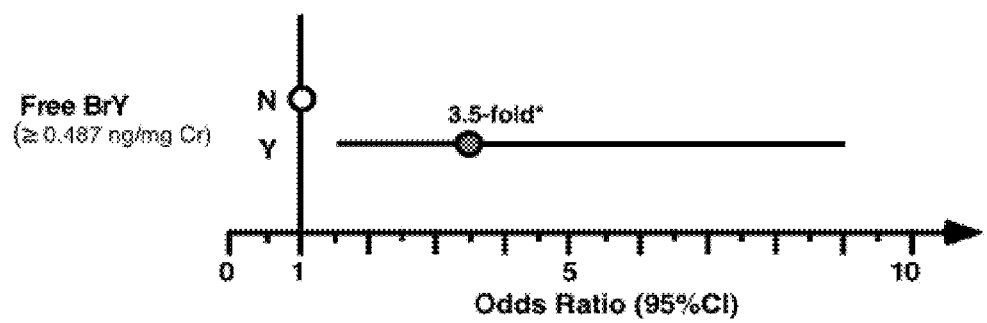
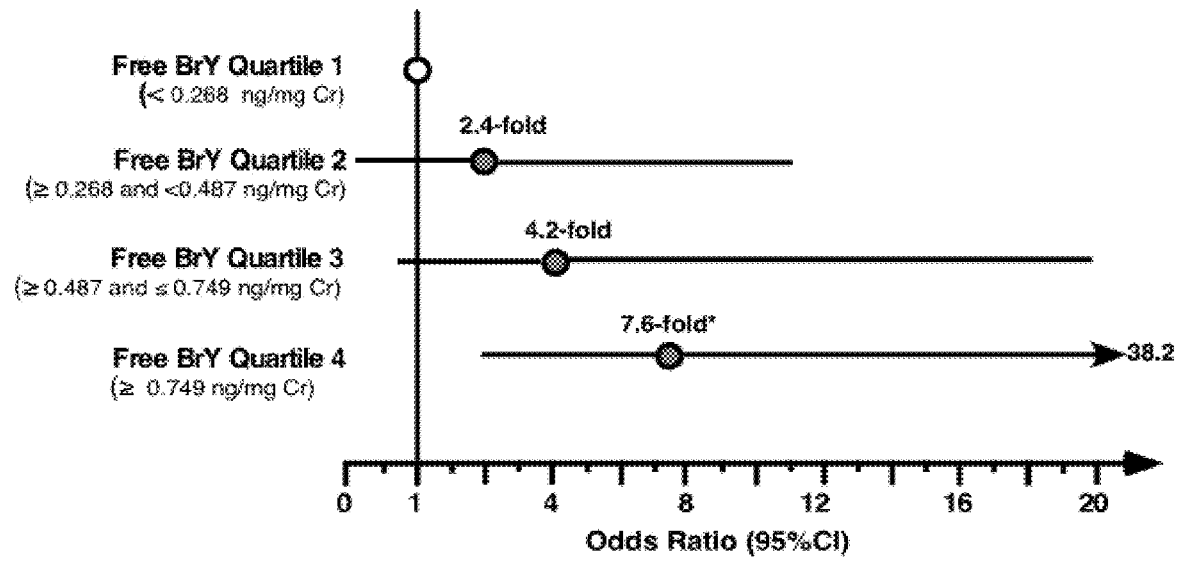
FIG. 4C

FIG. 4B
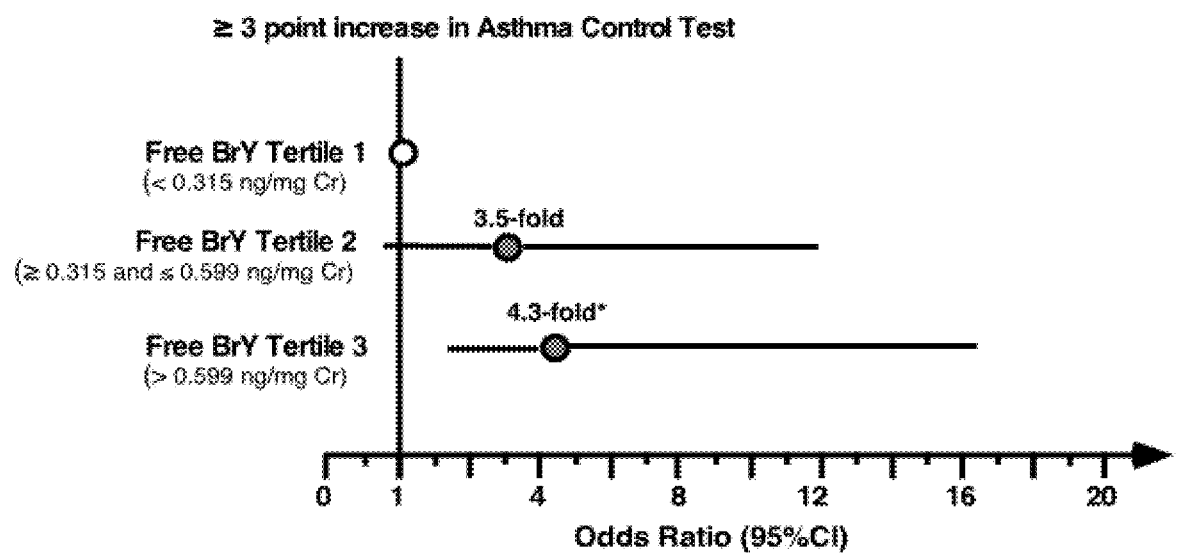
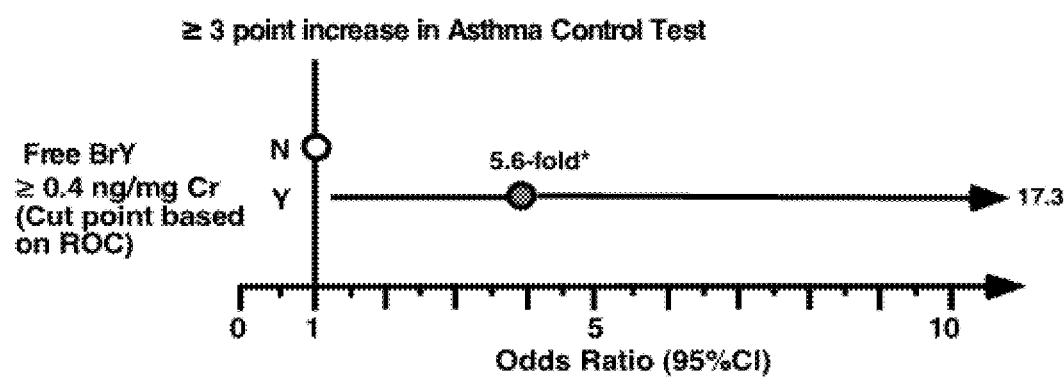
FIG. 4D

FIG. 5A
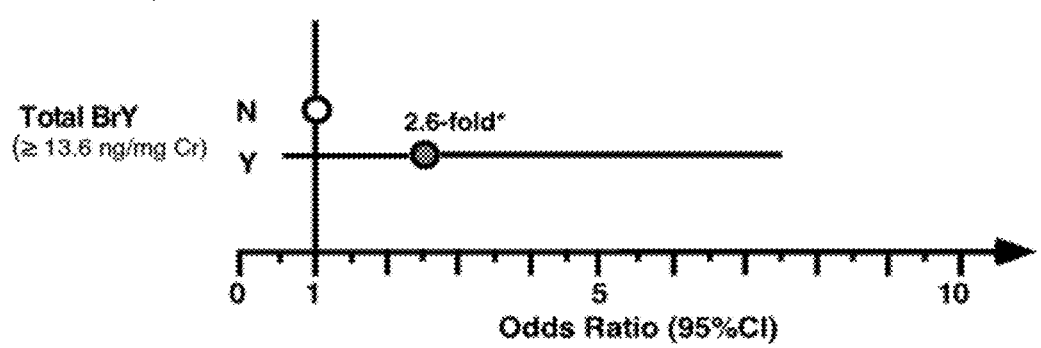
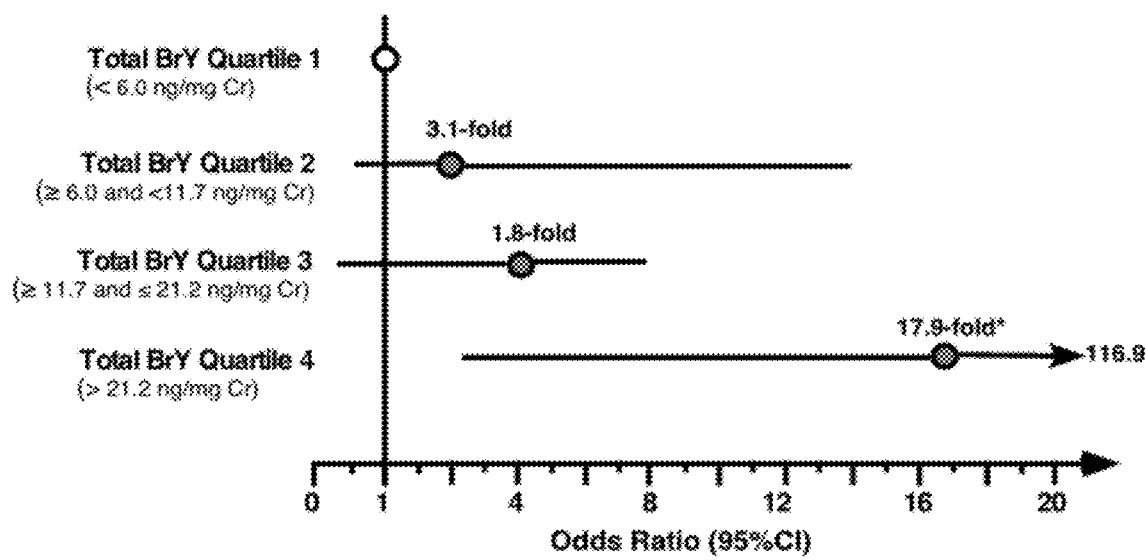
FIG. 5C

A.

B.

DETECTION OF GLUCURONIDATED AND 3-BROMOTYROSINE

This application is a divisional of U.S. patent application Ser. No. 16/281,811 filed Feb. 21, 2019, now U.S. Pat. No. 11,249,091, which claims priority to U.S. Provisional Application Ser. No. 62/633,693, filed Feb. 22, 2018, each of which is herein incorporated by reference in its entirety.

This invention was made with government support under HL 103453 awarded by the National Institutes of Health. The government has certain rights in the invention.

FIELD OF THE INVENTION

The present invention relates to methods, kits, and compositions for: i) detecting the level of 3-bromotyrosine in a sample that has been treated to liberate 3-bromotyrosine from 4-O-glucuronide-3-bromotyrosine, and/or ii) detecting the level of 4-O-glucuronide-3-bromotyrosine, and/or the combined level of both 4-O-glucuronide-3-bromotyrosine and 3-bromotyrosine, in a sample that has not been treated to liberate 3-bromotyrosine from 4-O-glucuronide-3-bromotyrosine. In certain embodiments, such detected levels are used to: i) identify the presence, severity, or risk of an eosinophilic disorder (e.g., asthma or a TH2-high eosinophilic disorder); ii) identify therapy effective for treating asthma or an eosinophilic disorder; or iii) identify patients suitable for treatment with therapeutic agents targeted to asthma or an eosinophilic disorder.

BACKGROUND

Asthma affects a wide spectrum of individuals with diverse immunological and biochemical endotypic responses that lead to a variety of asthma phenotypes. Despite the recognized heterogeneity of asthma, treatment is prescribed equally to all patients in a uniformly applied stepped-care approach. Current practice relies on subjective symptoms, asthma control tests, or measure of airflow obstruction to add on, or step down therapy. This approach is post-hoc, and often results in under- and/or over-treatment. The morbidities and costs associated with this common disease and the lack of ability to finely tune care provide the imperative to develop personalized medicine approaches aimed at underlying mechanisms. Quantifiable non-invasive biomarkers that are informative for asthma control and airway inflammation are needed for personalized asthma treatment plans and will be essential in planning therapies and assessing efficacy of biologics such as anti-IgE, anti-IL5, and others. But, in the absence of appropriately sensitive tests to identify responder endotypes, patients will not fully realize the benefits of these new therapies.

Eosinophils in blood and sputum are used as cellular biomarkers of atopic, or TH2-high asthma. Eosinophils are present in increased numbers in airways of atopic asthmatics and produce much more ROS than cells found in healthy lungs. Early studies showed that the amount of ROS generated by eosinophils is directly correlated to the severity of hyperreactivity in asthma patients. Experimental exposure of atopic asthmatics to allergen, or asthma exacerbations, leads to even greater amounts of superoxid. Studies 30 years ago showed heterogeneity among eosinophils within asthma. Hypodense eosinophils were more active than normodense eosinophils, had twice as much eosinophil peroxidase activity, and comprised ~20-80% of circulating eosinophils in asthma. The hypodense eosinophil could be produced by exposure to IL-5 in vitro or in response to antigen in vivo. Unfortunately, its measure was laborious, and so clinicians turned to total blood eosinophils as a surrogate of the hypodense eosinophil, although it was recognized that asthma severity was better reflected by the numbers of hypodense eosinophils.

SUMMARY OF THE INVENTION

The present invention relates to methods, kits, and compositions for: i) detecting the level of 3-bromotyrosine in a sample that has been treated to liberate 3-bromotyrosine from 4-O-glucuronide-3-bromotyrosine, and/or ii) detecting the level of 4-O-glucuronide-3-bromotyrosine, and/or the combined level of both 4-O-glucuronide-3-bromotyrosine and 3-bromotyrosine, in a sample that has not been treated to liberate 3-bromotyrosine from 4-O-glucuronide-3-bromotyrosine. In certain embodiments, such detected levels are used to: i) identify the presence, severity, or risk of an eosinophilic disorder (e.g., asthma or a TH2-high eosinophilic disorder); ii) identify therapy effective for treating asthma or an eosinophilic disorder; or iii) identify patients suitable for treatment with therapeutic agents targeted to asthma or an eosinophilic disorder.

In some embodiments, provided herein are methods of testing a sample comprising: a) testing a first sample from a subject to determine the level of 3-bromotyrosine, wherein the first sample has been treated to liberate 3-bromotyrosine from 4-O-glucuronide-3-bromotyrosine; and/or b) testing a second sample from the subject to determine: A) the level of 4-O-glucuronide-3-bromotyrosine, and/or B) the combined level of both 4-O-glucuronide-3-bromotyrosine and 3-bromotyrosine, wherein the second sample has not been treated to liberate 3-bromotyrosine from 4-O-glucuronide-3-bromotyrosine.

In particular embodiments, provided herein are methods of identifying the presence, severity, risk of, or risk of exacerbation of asthma or an eosinophilic disorder in a subject comprising: a) performing at least one of the following: i) testing a first sample from a subject to determine the level of 3-bromotyrosine, wherein the first sample has been treated to liberate 3-bromotyrosine from 4-O-glucuronide-3-bromotyrosine; and/or ii) testing a second sample from the subject to determine: A) the level of 4-O-glucuronide-3-bromotyrosine, and/or B) the combined level of both 4-O-glucuronide-3-bromotyrosine and 3-bromotyrosine, wherein the second sample has not been treated to liberate 3-bromotyrosine from 4-O-glucuronide-3-bromotyrosine; and b) identifying the presence, severity, risk of, or risk of exacerbation of asthma or an eosinophilic disorder in the subject based on: i) an elevated level of the 3-bromotyrosine in the first sample compared to a control, ii) an elevated level of 4-O-glucuronide-3-bromotyrosine in the second sample compared to a control; and/or iii) an elevated combined level of 4-O-glucuronide-3-bromotyrosine and 3-bromotyrosine in the second sample compared to a control.

In certain embodiments, provided herein are methods of treating a subject comprising: a) performing at least one of the following: i) identifying a subject as having an elevated level of 3-bromotyrosine in a first sample from the subject which was tested to determine the level of 3-bromotyrosine, wherein the first sample had been treated to liberate 3-bromotyrosine from 4-O-glucuronide-3-bromotyrosine; and/or ii) identifying a subject as having an elevated level of 4-O-glucuronide-3-bromotyrosine in a second sample, and/or an elevated combined level of both 4-O-glucuronide-3-bromotyrosine and 3-bromotyrosine in the second sample, wherein the second sample was tested to determine the level of 4-O-glucuronide-3-bromotyrosine or both 4-O-glucuronide-3-bromotyrosine and 3-bromotyrosine, and wherein the second sample had not been treated to liberate 3-bromotyrosine from 4-O-glucuronide-3-bromotyrosine; and b) treating the subject with a therapeutic agent used to treat asthma or an eosinophilic disorder.

In some embodiments, provided herein are methods of screening a candidate therapeutic agent comprising: a) performing at least one of the following: i) testing a first sample from a subject to determine the level of 3-bromotyrosine, wherein the first sample has been treated to liberate 3-bromotyrosine from 4-O-glucuronide-3-bromotyrosine; and/or ii) testing a second sample from the subject to determine: A) the level of 4-O-glucuronide-3-bromotyrosine, and/or B) the combined level of both 4-O-glucuronide-3-bromotyrosine and 3-bromotyrosine, wherein the second sample has not been treated to liberate 3-bromotyrosine from 4-O-glucuronide-3-bromotyrosine; and b) performing at least one of the following after a subject has received a candidate therapeutic agent for asthma and/or an eosinophilic disorder: i) testing a third sample from a subject to determine the level of 3-bromotyrosine, wherein the third sample has been treated to liberate 3-bromotyrosine from 4-O-glucuronide-3-bromotyrosine; and/or ii) testing a fourth sample from the subject to determine: A) the level of 4-O-glucuronide-3-bromotyrosine, and/or B) the combined level of both 4-O-glucuronide-3-bromotyrosine and 3-bromotyrosine, wherein the fourth sample has not been treated to liberate 3-bromotyrosine from 4-O-glucuronide-3-bromotyrosine. In further embodiments, the method further comprise: c) identifying the candidate therapeutic agent as efficacious based on: i) a decrease in the level of the 3-bromotyrosine from the first sample to the third sample, ii) a decrease in the level of the 4-O-glucuronide-3-bromotyrosine in the fourth sample compared to the second sample; and/or iii) a decrease in the combined level of 4-O-glucuronide-3-bromotyrosine and 3-bromotyrosine in the second sample compared to the fourth sample. In further embodiments, the methods further comprise: administering the efficacious therapeutic agent after step c). In other embodiments, the methods further comprise c) identifying the candidate therapeutic agent as non-efficacious based on: i) no decrease in the level of the 3-bromotyrosine from the first sample to the third sample, ii) no decrease in the level of the 4-O-glucuronide-3-bromotyrosine in the fourth sample compared to the second sample; and/or iii) no decrease in the combined level of 4-O-glucuronide-3-bromotyrosine and 3-bromotyrosine in the second sample compared to the fourth sample.

In some embodiments, provided herein are compositions, systems, and kits comprising: a) a sample from a subject having, or suspected of having, asthma and/or a eosinophilic disorder; and b) a de-glucuronidation agent. In certain embodiments, the de-glucuronidation agent comprises an enzyme that catalyzes removal of a glucuronide moiety (e.g., β-glucuronidase), an acid, or a base (e.g., to promote hydrolysis).

In certain embodiments, provided herein are compositions, systems, and kits comprising: a) a sample from a subject having, or suspected of having, asthma and/or a eosinophilic disorder; and b) a detection agent configured to bind to 4-O-glucuronide-3-bromotyrosine. In certain embodiments, the detection agent comprises an antibody or antigen binding portion thereof directed against 4-O-glucuronide-3-bromotyrosine. In further embodiments, the detection agent is detectably labeled (e.g., with a fluorophore or chromophore).

In some embodiments, provided herein are systems and kits comprising: a) a report that indicates a subject has been: i) identified as having an elevated level of 3-bromotyrosine in a first sample from the subject which was tested to determine the level of 3-bromotyrosine, wherein the first sample had been treated to liberate 3-bromotyrosine from 4-O-glucuronide-3-bromotyrosine; and/or ii) identified as subject having an elevated level of 4-O-glucuronide-3-bromotyrosine in a second sample, and/or an elevated combined level of both 4-O-glucuronide-3-bromotyrosine and 3-bromotyrosine in the second sample, wherein the second sample was tested to determine the level of 4-O-glucuronide-3-bromotyrosine or both 4-O-glucuronide-3-bromotyrosine and 3-bromotyrosine, and wherein the second sample had not been treated to liberate 3-bromotyrosine from 4-O-glucuronide-3-bromotyrosine; and b) a therapeutic agent used to treat asthma or an eosinophilic disorder.

In some embodiments, provided herein are compositions, systems, and kits comprising: a) at least one of the following internal standards: i) stable isotope labeled 3-bromotyrosine molecules, and/or ii) stable isotope labeled 4-O-glucuronide-3-bromotyrosine molecules; and b) at least one of the following: i) a de-glucuronidation agent (e.g., an enzyme that catalyzes removal of a glucuronide moiety, acid, or base); ii) a detection agent configured to bind to 4-O-glucuronide-3-bromotyrosine; iii) a sample from a subject having, or suspected of having, asthma and/or a eosinophilic disorder. In particular embodiments, the stable isotope labeled 3-bromotyrosine molecules comprise 13C6 labeled 3-bromotyrosine (see, FIG. 12A). In other embodiments, the stable isotope labeled 4-O-glucuronide-3-bromotyrosine molecules comprise 13C6 labeled 4-O-glucuronide-3-bromotyrosine (see, FIG. 12B). In some embodiments of the kits and systems, all or at least some of the reagent are located in separate containers (e.g., which are further packaged in a container, such as a box or bag). In other embodiments, all or most of the recited components are present in the composition, or kit, or system.

In some embodiments, the first and/or second sample is from a subject with, or suspected of having, asthma and/or an eosinophilic disorder. In other embodiments, the first sample has been treated with a de-glucuronidation agent (e.g., an enzyme that catalyzes removal of a glucuronide moiety, an acid, or a base) or procedure (e.g., acid or base for hydrolysis, optionally in the presence of heat). In some embodiments, the de-glucuronidation agent comprises β-glucuronidase. In particular embodiments, the testing the first and/or second sample comprises performing a detection method selected from: mass spectrometry, an immunological assay, HPLC-UV/VIS, LC-Electrochemical detection, or LC-Ampimetric detection method. In some embodiments, the first sample and the second sample originate from the same initial sample taken from the subject. In other embodiments, the first sample and the second sample originate from different initial samples taken from the subject (e.g., one is a urine sample and one is a serum sample; or one is a urine sample at a first time and the one is a urine sample at a different time). In certain embodiments, the first and/or second samples comprises a sample type selected from: urine, saliva, serum, plasma, tissue biopsy, and whole blood.

In some embodiments, the presence, severity, risk of, or risk of exacerbation of asthma is identified in the subject. In other embodiments, the presence, severity, risk of, or risk of an eosinophilic disorder is identified in the subject.

In certain embodiments, the subject, prior to step a) is identified as having or being at risk of asthma and/or an eosinophilic disorder. In further embodiments, the methods herein comprise: c) treating the subject with a therapeutic agent used to treat asthma or an eosinophilic disorder. In other embodiments, the methods further comprise: c) generating, transmitting, and/or graphically displaying (e.g., on paper or on a computer screen) a report that indicates the 3-bromotyrosine levels from the first sample, and/or the 4-O-glucuronide-3-bromotyrosine from the second sample, and/or the combined level of both 4-O-glucuronide-3-bromotyrosine and 3-bromotyrosine from the second sample, are elevated compared to corresponding controls, and that the subject is in need of a therapeutic agent used to treat asthma or an eosinophilic disorder. In additional embodiments, the methods herein further comprise: c) generating, transmitting, and/or graphically displaying (e.g., on paper or on a computer screen) a report that indicates the 3-bromotyrosine levels from the first sample, and/or the 4-O-glucuronide-3-bromotyrosine from the second sample, and/or the combined level of both 4-O-glucuronide-3-bromotyrosine and 3-bromotyrosine from the second sample, are elevated compared to corresponding controls, and that the subject has or is at risk of asthma and/or an eosinophilic disorder. In other embodiments, the methods herein comprise: c) characterizing the subject as having asthma and/or an eosinophilic disorder, based on finding elevated levels of the 3-bromotyrosine levels from the first sample, and/or the 4-O-glucuronide-3-bromotyrosine from the second sample, and/or the combined level of both 4-O-glucuronide-3-bromotyrosine and 3-bromotyrosine from the second sample.

In some embodiments, the first and/or second sample is from a subject with, or suspected of having, asthma and/or an eosinophilic disorder. In other embodiments, the first sample has been treated with a de-glucuronidation agent (e.g., acid, base, or an enzyme that catalyzes removal of a glucuronide moiety) and/or de-glucuronidation procedure (e.g., heating the sample in presence of acid or base). In certain embodiments, the de-glucuronidation agent comprises β-glucuronidase.

In some embodiments, the testing the first and/or second sample comprises performing a detection method selected from: mass spectrometry, an immunological assay, HPLC-UV/VIS, LC-Electrochemical detection, or LC-Ampimetric detection method. In other embodiments, the first sample and the second sample originate from the same initial sample taken from the subject. In additional embodiments, the first sample and the second sample originate from different initial samples taken from the subject. In additional embodiments, the first and/or second samples comprises a sample type selected from: urine, saliva, serum, plasma, tissue biopsy, and whole blood.

In certain embodiments, the methods herein further comprise informing the subject that they have asthma and/or an eosinophilic disorder, the severity of the asthma and/or the eosinophilic disorder, and/or the risk of exacerbating the asthma and/or the eosinophilic disorder. In particular embodiments, the severity of asthma includes: i) declining lung function, or ii) stable, non-declining lung function.

In particular embodiments, the control level or combined control level is determined or pre-determined from: i) a sample from the subject when not suffering from symptoms of asthma or an eosinophilic disorder, ii) a sample from a person, or sample from a plurality of people, without asthma or an eosinophilic disorder, iii) samples from the general population. In certain embodiments, the candidate therapeutic agent herein is selected from the group consisting of: Mepolizumab, Reslizumab, Benralizumab, Lebrikizumab, Tralokinumab, pitrakinra, Dupilumab, a leukotriene receptor antagonist (LTRA), a steroidal asthma drug, a non-steroidal asthma drug, a corticosteroid, prednisone, and budesonide. In other embodiments, the identifying is based on viewing, hearing, or receiving a paper or electronic report.

DESCRIPTION OF THE FIGURES

FIGS. 4A-D. ORs and 95% Cl for baseline free BrTyr (ng/mg Cr) and a positive clinical outcome (3 point or greater asthma control test response) to mepolizumab. Results shown represent the ORs (filled circles) and 95% Cl (lines) Asterisk indicates P<0.05 as determined by likelihood-ratio c test. Free urinary BrTyr levels predict dose dependent risk for asthma presence and severity. And correspondingly, those with higher levels of urinary BrTyr at baseline are dose dependently more likely to show improvement in their asthma severity questionnaire (Asthma Control Test) following 3 months of mepolizumab therapy. FIG. 4A, BrTyr is stratified by above v below median value; FIG. 4B by tertiles; FIG. 4C by quartiles; and FIG. 4D BrTyr is stratified by ROC curve cut-point.

FIGS. 5A-D. ORs and 95% Cl for baseline free BrTyr (ng/mg Cr) and a positive clinical outcome (3 point or greater asthma control test response) to mepolizumab. Results shown represent the ORs (filled circles) and 95% Cl (lines) Asterisk indicates P<0.05 as determined by likelihood-ratio c test. Because so much of the BrTyr is glucuronidated, after enzyme digestion and release, the level of Total BrTyr quantified is 10-20 fold higher than that of free BrTyr, and correspondingly, is much more accurately measured. Thus, one sees stronger and cleaner clinical signals when examining those with higher levels of urinary Total BrTyr at baseline. Total BrTyr predicts dose dependent improvement in asthma severity questionnaire (Asthma Control Test) in response to 3 months of mepolizumab therapy. FIG. 5A stratified by above v below median value. FIG. 5B by tertiles, FIG. 5C by quartiles, and FIG. 5D by ROC curve cut-point.

DEFINITIONS

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION

The present invention relates to methods, kits, and compositions for: i) detecting the level of 3-bromotyrosine in a sample that has been treated to liberate 3-bromotyrosine from 4-O-glucuronide-3-bromotyrosine, and/or ii) detecting the level of 4-O-glucuronide-3-bromotyrosine, and/or the combined level of both 4-O-glucuronide-3-bromotyrosine and 3-bromotyrosine, in a sample that has not been treated to liberate 3-bromotyrosine from 4-O-glucuronide-3-bromotyrosine. In certain embodiments, such detected levels are used to: i) identify the presence, severity, or risk of an eosinophilic disorder (e.g., asthma or a TH2-high eosinophilic disorder); ii) identify therapy effective for treating asthma or an eosinophilic disorder; or iii) identify patients suitable for treatment with therapeutic agents targeted to asthma or an eosinophilic disorder.

Work conducted during development of embodiments described herein revealed that urinary free bromotyrosine, which for more than a decade has been used as a marker of eosinophil activation, represents only a minor component of the BrTyr formed during eosinophil activation. Most of the BrTyr is, in fact, metabolized and glucuronidated, forming 4-O-glucuronide-3-bromotyrosine. Consequently, only a small proportion (~5%) of BrTyr is present in its free form in urine, while the majority is glucuronidated in urine. It was found that by liberating BrTyr via enzyme digestion, one can generate a signal that is, for example, about 20-fold higher, and generally easier to monitor analytically for measurement.

Figure 10:
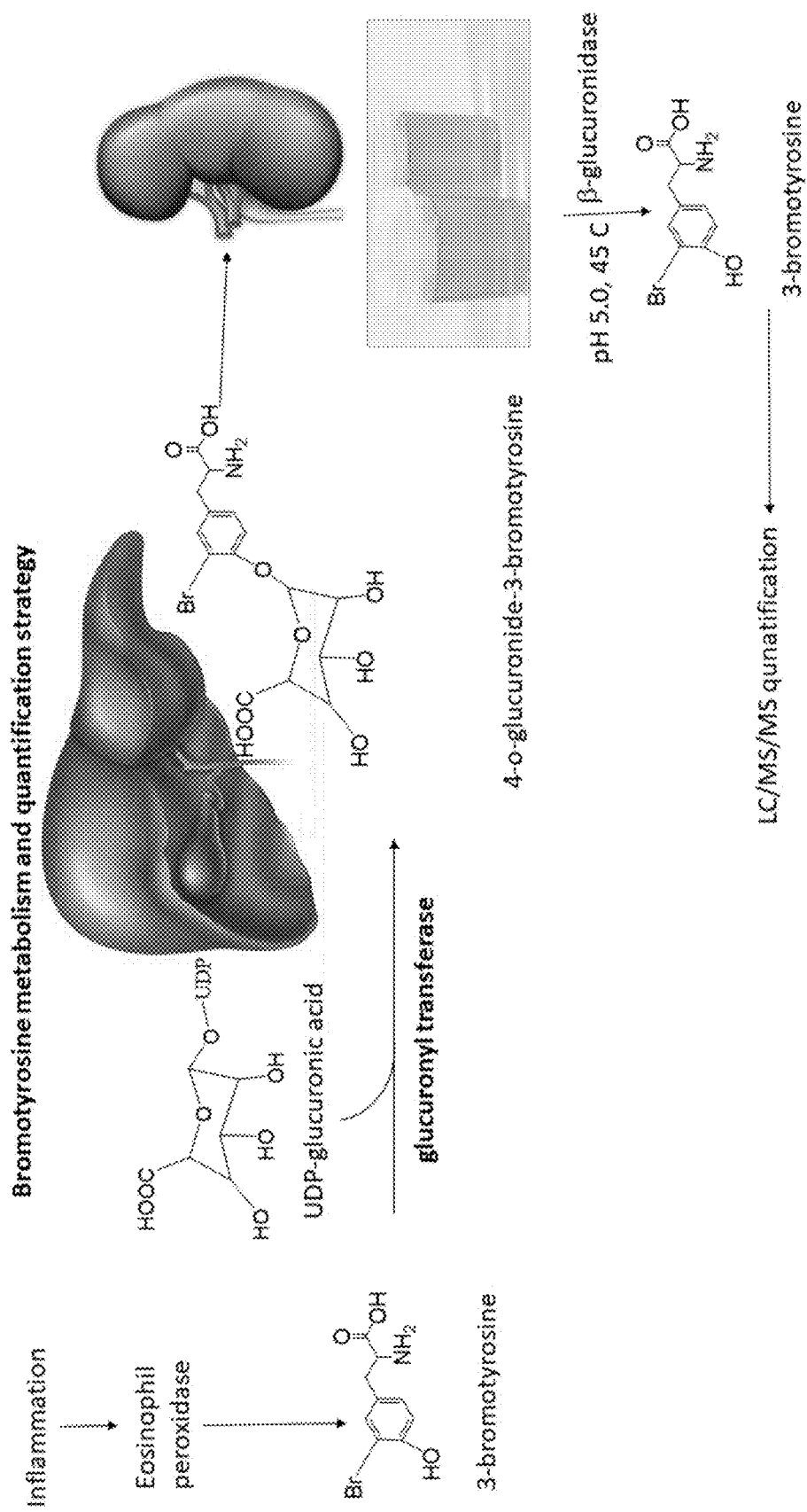
FIG. 10 bromotyrosine metabolism and exemplary quantification method.
Figure 11:
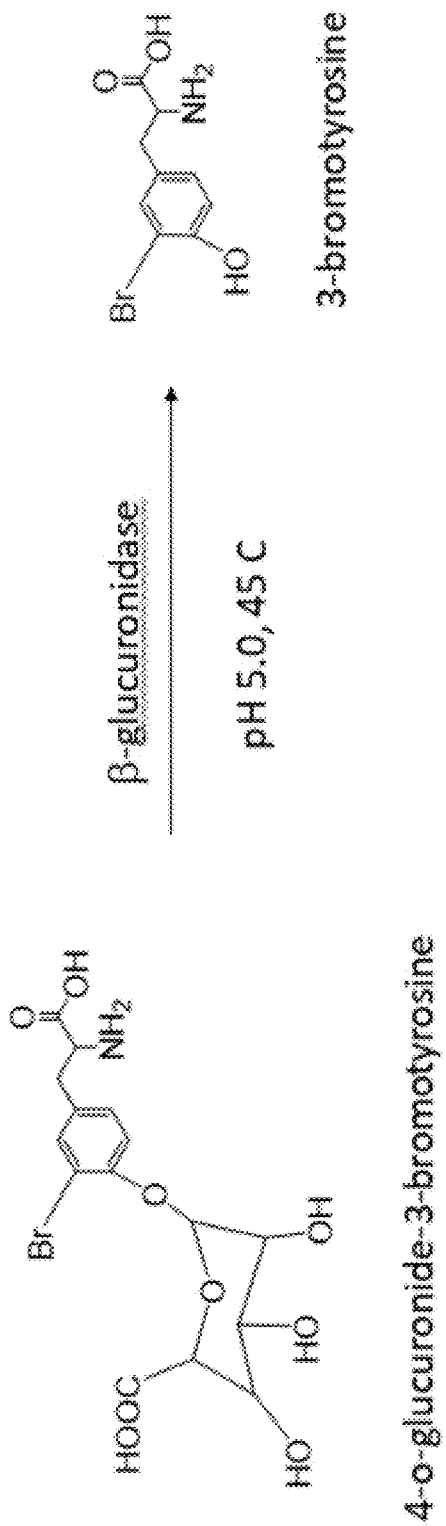
FIG. 11 shows how β-glucuronidase catalyzes hydrolysis of 4-o-glucuronide-3-bromotyrosine.

Work conducted during the development of embodiment described herein found that bromotyrosine (BrTyr) (as shown in FIGS. 10-11) is metabolized into a glucuronidated form, 4-O-glucuronide-3-bromotyrosine (see FIGS. 10-11), whose level is much larger than free BrTyr, and which is highly variable and poorly correlated with free BrTyr. In certain embodiments, to get a true quantification of Total BrTyr, one can enzymatically digest (or otherwise treat) a sample (e.g., urine, saliva, plasma, serum, blood, etc.) with β-glucuronidase, to promote hydrolysis of the 4-O-glucuronide-3-bromotyrosine, releasing free BrTyr. Thus, in some embodiments, measurement of "Total" BrTyr in post de-glucuronidated (e.g., glucuronidase digested) samples yields a sum of the free BrTyr (i.e., naturally present as free BrTyr), plus all the glucuronidated BrTyr. The methods, systems, kits, and compositions herein are not limited by the agent or procedure used to de-glucuronidate 4-O-glucuronide-3-bromotyrosine to liberate free BrTyr. In certain embodiments, reagents and procedures are employed that do not employ acid, to avoid producing artifactual BrTyr, which can be generated under such acidic conditions.

In work conducted during development of embodiments described herein, is was found that certain urine samples contained approximately 5% Free BrTyr (which is non-glucuronidated Bromotyrosine and is as shown in FIGS. 10-11), and that approximately 95% BrTyr is 4-O-glucuronide-3-bromotyrosine. Therefore, "total BrTyr" refers to naturally free BrTyr+glucuronidase (or other de-glucuronidation agent) treated 4-O-glucuronide-3-bromotyrosine. In certain embodiments, liberating 3-bromotyrosine from glucuronidated BrTyr via enzyme digestion (or other de-glucuronidation agent) provides Total Bromotyrosine whose signal is approximately 10-20-fold higher than free BrTyr (e.g., 10 times . . . 15 times . . . 18 times . . . 20 times . . . or 25 times higher). In certain embodiments, detection of 4-O-glucuronide-3-bromotyrosine or total BrTyr (e.g., in a de-gluroronidating agent treat sample), is employed to assess disease risk and/or monitor or design therapy for such diseases and conditions such as asthma, or a TH2-high eosinophil-rich disease, such as eosinophilic granulomatosis with polyangiitis (previously Churg-Strauss Disease), Eosinophilic Esophagitis, Eosinophilic Gastritis, Eosoniphilic Colitis, Eosinophilic Enteritis, Hypereosinophilic syndrome (blood or organ) or other eosinophilic proliferative disorders.

The present invention is noted limited to any particular method to detect 4-O-glucuronide-3-bromotyrosine and 3-bromotyrosine. For example, 4-O-glucuronide-3-bromotyrosine and 3-bromotyrosine can be measured using any suitable methodology, including but not limited, to mass spectrometry, HPLC/UV, HPLC/Vis, LC/MS/MS, immunological detection methods. In other embodiments, 4-O-glucuronide-3-bromotyrosine and 3-bromotyrosine are measured using: 1) a sandwich immunoassay (e.g., monoclonal, polyclonal and/or DVD-Ig sandwich immunoassays or any variation thereof (e.g., monoclonal/DVD-Ig or DVD-Ig/polyclonal), including chemiluminescence detection, radioisotope detection (e.g., radioimmunoassay (RIA)) and enzyme detection (e.g., enzyme immunoassay (EIA) or enzyme-linked immunosorbent assay (ELISA) (e.g., Quantikine ELISA assays, R&D Systems, Minneapolis, Minn.))), 2) a competitive inhibition immunoassay (e.g., forward and reverse), 3) a fluorescence polarization immunoassay (FPIA), 4) an enzyme multiplied immunoassay technique (EMIT), 5) a bioluminescence resonance energy transfer (BRET), 6) a homogeneous chemiluminescent assay, 7) a SELDI-based immunoassay, 8) chemiluminescent microparticle immunoassay (CMIA) and 9) a clinical chemistry colorimetric assay (e.g., IMA, creatinine for eGFR determination and LC-MS/MS). (See, e.g., Tietz Textbook of Clinical Chemistry and Molecular Diagnostics. 4th Edition, edited by C A Burtis, E R Ashwood and D E Bruns, Elsevier Saunders, St. Louis, Mo., 2006.).

Further, if an immunoassay is being utilized, any suitable detectable label as is known in the art can be used. For example, the detectable label can be a radioactive label (such as 3H, 125I, 35S, 14C, 32P, and 33P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous or heterogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In certain embodiments, 4-O-glucuronide-3-bromotyrosine is detected with one antibody or antibody fragment that recognizes the 3-bromotyrosine moiety (e.g., as part of immunocapture), and then a glucose oxidase reaction is initiated to generate H2O2 from the 4-O-glucuronide moiety. A peroxidase coupled reagent is then employed to visualize the color reaction.

In certain embodiments, 4-O-glucuronide-3-bromotyrosine and/or 3-bromotyrosine are detected by one of the following methods: i) HPLC with electrochemical detection; ii) HPLC with Ampimetric detection; iii) HPLC with UV/VIS detection; and iv) derivitization and GC/MS detection.

Figure 12:
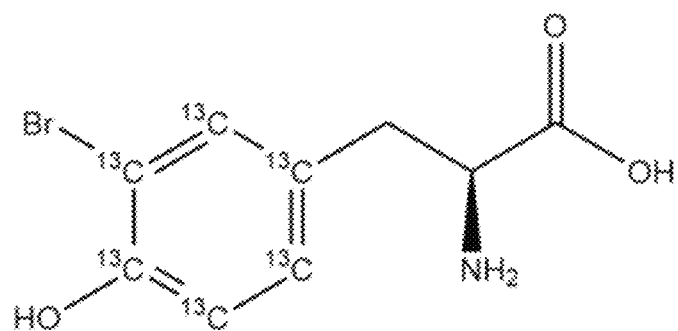
FIG. 12. Panel A shows 13C6 labeled 3-bromotyrosine. Panel B shows 13C6 labeled 4-O-glucuronide-3-bromotyrosine.
Figure 12:
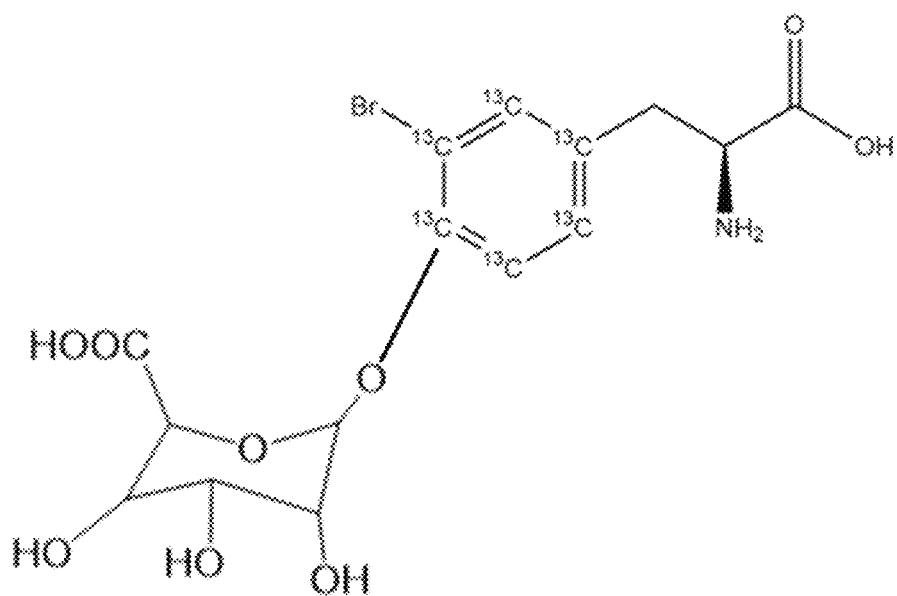
Figure 13:
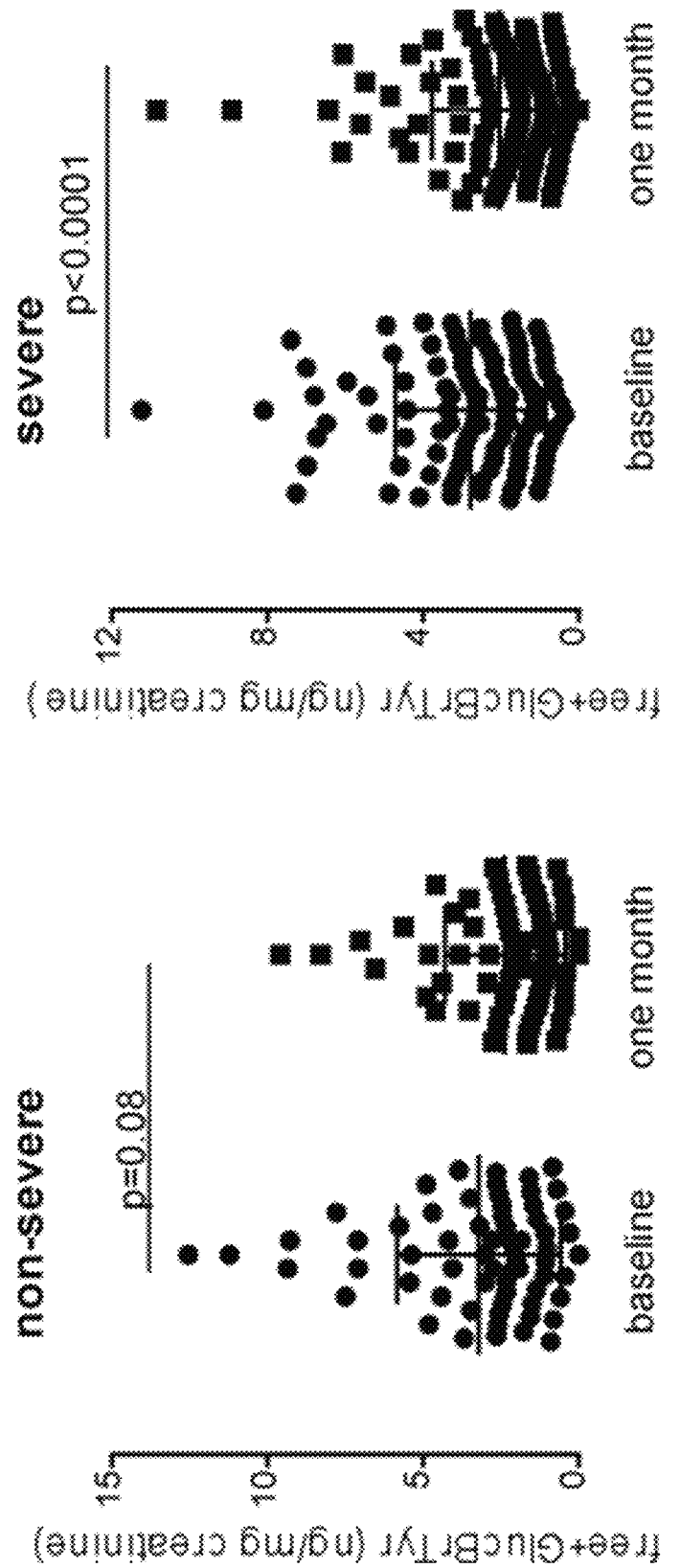
FIG. 13 shows a scatter plot of urine free 3-bromotyrosine (BrY) after glucuronidase incubation in non-severe asthmatic patients (n=65, left panel) and severe asthmatic patients (n=120, right panel) at baseline vs one month's medication (40 mg injected Triamcinolone with mean±SD indicated. BrY was quantified by LC/MS/MS with $^{13}C_6$—BrY as internal standard and expressed as per mg creatinine. P value was calculated by Wilcoxon Rank Sum test.

In some embodiments, 4-O-glucuronide-3-bromotyrosine and/or 3-bromotyrosine are detected by methods employing mass spectrometry. Exemplary mass detection methods for 3-bromotyrosine are described in Example 1 below. 4-glucuronide-3-bromotyrosine can be monitored, for example, by LC/ESI/MS/MS in positive MRM mode directly with parent to daughter transitions: m/z 436>390, 436>311, 438>392, 438>311. In certain embodiments, stable isotope labeled 3-bromotyrosine molecules, and/or stable isotope labeled 4-O-glucuronide-3-bromotyrosine internal standards are employed (see, e.g., FIG. 12). In certain embodiments, 3-bromotyrosine is detected in urine employing methods described in the art (e.g., using LC/EST/MS/MS) as described in Wedes et al., Clin Transl Sci. 2009 Apr.; 2(2):112-7 and Wedes et al., J Pediatr., 2011 Aug.; 159(2): 248-55.e1, both of which are herein incorporated by reference in their enteritis, specifically for the mass spectrometric detection methods described therein).

In certain embodiments, as part of the methods of the present invention, a patient is administered or recommended for administration of a therapeutic agent. Examples of such agents include, for example: Mepolizumab/Nucala (GSK anti-IL5); Reslizumab (Cinquil™, Teva Pharmaceuticals; formerly SCH-55700 anti-IL5); Benralizumab (a humanized afucosylated IgG1κ mAb to human IL-5Rα); Lebrikizumab (anti-IL-13, Genentech/Chugai Pharmaceutical); Tralokinumab (CAT-354, MedImmune; an injectable anti-IL-13 humanized IgG4 mAb); a recombinant human IL-4 variant called pitrakinra (Aerovant™, Aerovance; which competitively inhibits the IL-4Rα receptor complex to interfere with the actions of both IL-4 and IL-13); Dupilumab (SAR231893/REGN668; which is a fully humanized mAb to the IL-4Rα/IL-13Rα1 receptor complex that inhibits both IL-4 and IL-13 signaling); a leukotriene receptor antagonist (LTRA); a steroidal drug (e.g., as shown in Table 5); and a non-steroidal drug (e.g., as shown in Table 6). In certain embodiments, the therapeutic agent is a TH2-targeted biologic therapy, such as those targeting pathways of: IL4, IL5, IL13, IL17/25. In some embodiments, anti-IgE therapy is employed. Additional examples of therapeutic agents (e.g., for treating an eosinophilic disorder) include, but are not limited to: corticosteroids (e.g., prednisone), Flovent, and budesonide.

TABLE 5

Steroidal Drugs

| Generic Name | Chemical Name | Brand Name |
| --- | --- | --- |
| Beclomethasone Dipropionate HFA | 9-chloro-11β,17,21-trihydroxy-16βmethylpregna-1,4-diene-3, 20-dione 17,21-dipropionate. | QVAR Inhalation Aerosol 40 mcg/puff & 80 mcg/puff |
| Budesonide | 16,17-(butylidenebis(oxy))-11,21-dihydroxy-, (11-β,16-α)-pregna-1,4-diene-3,20-dione | Plumicort Flexhaler & Plumicort Respules |
| Budesonide in combination with Formoterol | (RS)-11β, 16α, 17,21-Tetrahydroxypregna-1,4-diene-3,20-dione cyclic 16,17-acetal with butyraldehyde (Budesonide) (R*,R*)-(±)-N-[2-hydroxy-5-[1-hydroxy-2-[[2-(4-methoxyphenyl)-1-methylethyl]amino]ethyl]phenyl]formamide, (E)-2-butendioate(2:1), dihydrate | Symbicort |

TABLE 5-continued

| Steroidal Drugs | | |
|---|---|---|
| Generic Name | Chemical Name | Brand Name |
| Ciclesonide | 2-[(1S, 2S, 4R, 8S, 9S,11S, 12S, 13R)-6-cyclohexyl-11-hydroxy-9, 13-dimethyl-16-oxo-5, 7-dioxapentacyclo [10.8.0.02,9.04, 8.013,18] icosa-14, 17-dien-8-yl]- 2-oxoethyl 2-methylpropanoate | Alvesco Inhalation Aerosol |
| Flunisolide | (1S,2S,4R,8S,9S,11S,12S,13R,19S)-19-fluoro-11-hydroxy-8-(2-hydroxyacetyl)-6,6,9,13-tetramethyl-5,7-dioxapentacyclo[10.8.0.02,9.04,8.013,18] icosa-14,17-dien-16-one | Aerobid Aerosol and Aerobid-M Aerosol |
| Fluticasone Propionate | S-(fluoromethyl)-6α,9-difluoro-11β, 17-dihydroxy-16α-methyl-3-oxoandrosta-1, 4-diene-17β-carbothioate, 17-propanoate | Flovent HFA and Flovent Diskus |
| Fluticasone in combination with Salmeterol (broncodialator) | S-(fluoromethyl)-6 α,9-difluoro-11 β, 17-dihydroxy-16α-methyl-3-oxoandrosta-1, 4-diene-17β-carbothioate, 17-propanoate [and] (RS)-2-(hydroxymethyl)-4-{1-hydroxy-2-[6-(4-phenylbutoxy)hexylamino]ethyl}phenol | Advair Diskus & Advair HFA |
| Mometasone furoate | (11β,16α)-9,21-dichloro-11-hydroxy-16-methyl-3,20-dioxopregna-1,4-dien-17-yl 2-furoate | Asmanex Twisthaler |
| Mometasone in combination with Formoterol (broncodialtor) | (11β,16α)-9,21-dichloro-11-hydroxy-16-methyl-3,20-dioxopregna-1,4-dien-17-yl 2-furoate [and] rac-(R,R)-N-[2-hydroxy-5-[1-hydroxy-2-[1-(4-methoxyphenyl)propan-2-ylamino]ethyl] phenyl]formamide | Dulera |
| Triamcinolone acetonide | (4aS,4bR,5S,6aS,6bS,9aR,10aS,10bS)-4b-fluoro-6b-glycoloyl-5-hydroxy-4a,6a,8,8-tetramethyl-4a,4b,5,6,6a,6b,9a,10,10a,10b,11,12-dodecahydro-2H-naphtho[2',1'1:4,5]indeno[1,2-d][1,3]dioxol-2-one | Azmacort Inhalation Aerosol |
| Prednisone | 17,21-dihydroxypregna-1,4-diene-3,11,20-trione | Deltasone |
| Prednisolone | (11β)-11,17,21-trihydroxypregna-1,4-diene-3,20-dione | |
| Methylprednisolone | (1S,2R,8S,10S,11S,14R,15S,17S)-14,17-dihydroxy-14-(2-hydroxyacetyl)-2,8,15-trimethyltetracyclo[8.7.0.02,7.011,15]heptadeca-3,6-dien-5-one | Medrol, Solu-Medrol, Depo-Medrol |
| Dexamethasone | (8S,9R,10S,11S,13S,14S,16R,17R)-9- Fluoro-11,17-dihydroxy-17-(2-hydroxyacetyl)-10,13,16- trimethyl-6,7,8,9,10,11,12,13,14,15,16,17- dodecahydro-3H-cyclopenta[a]phenanthren-1-one | Decadron |

TABLE 6

| Non-Steroidal Drugs | | | |
|---|---|---|---|
| Generic Name | Chemical Name | Brand Name | Type |
| Albuterol Sulfate | α1 [(tert-butylamino) methyl]-4-hydroxy-m-xylene-α, α'-diol sulfate (2:1) (salt) | VoSpireER Extended Release Tablets | LABA - recommended with use with steroids |
| Formoterol fumarate | ±)-2-hydroxy-5-[(1RS)-1-hydroxy-2-[[(1RS)-2-(4-methoxyphenyl)-1methylethyl] -amino]ethyl]formanilide fumarate dihydrate | Foradil Aerolizer | LABA - recommended with use with steroids |
| Salmeterol Xinafoate | ±-4-Hydroxy-α1 -[[[6-(4-phenylbutoxy)hexyl]amino]methyl]-1,3-benzenedimethanol compd. with 1-hydroxy-2-naphthalenecarboxylic acid (1:1) | Serevent Diskus | LABA - recommended with use with steroids |
| Albuterol Sulfate HFA | α1-[(tertbutylamino) methyl]-4-hydroxy-m-xylene-α,α'-diol sulfate (2:1) (salt) | ProAir HFA, Proventil HFA, Ventolin HFA | SABA - rescue medicine |
| Albuterol Sulfate Inhalation Solution | α1 [(tert-butylamino) methyl]-4-hydroxy-m-xylene-α, α'-diol sulfate (2:1) (salt) | | SABA - rescue medicine |
| Albuterol Sulfate Nebulizer Soluction | α1 [(tert-butylamino) methyl]-4-hydroxy-mxylene-α, α'-diol sulfate (2:1) (salt) | AccuNeb Inhalation Solution, Albuterol Sulfate 0.5% | SABA - rescue medicine |
| Ipratropium Bromide in combination with Albuterol Sulfate | [8-methyl-8-(1-methylethyl)- 8-azoniabicyclo[3.2.1] oct-3-yl] 3-hydroxy-2-phenyl-propanoate [and] α1 [(tert-butylamino) methyl]-4-hydroxy-mxylene-α, α'-diol sulfate (2:1) (salt) | Combivent; DuoNeb | Anticholinergic |

TABLE 6-continued

Non-Steroidal Drugs

| Generic Name | Chemical Name | Brand Name | Type |
|---|---|---|---|
| Ipratropium Bromide HFA | [8-methyl-8-(1-methylethyl)- 8-azoniabicyclo[3.2.1] oct-3-yl] 3-hydroxy-2-phenyl-propanoate | Atrovent, Apovent and Aerovent | Anticholinergic |
| Levalbuterol HCl | (R)-α1-[[(1,1-dimethylethyl)amino]methyl]-4-hydroxy-1,3-benzenedimethanol hydrochloride | Xopenex; Xopenex HFA | SABA - rescue medicine |
| Pirbuterol | (RS)-6-[2-(tert-butylamino)-1-hydroxyethyl]-2-(hydroxymethyl)pyridin-3-ol | Maxair Autoinhaler | SABA - rescue medicine |
| Tiotropium Bromide Inhalation Powder | (1α, 2β, 4 β, 5α, 7β)-7-[(Hydroxydi-2-thienylacetyl)oxy]-9,9-dimethyl-3-oxa-9-azoniatricyclo[3.3.1.02,4]nonane bromide monohydrate | Spiriva HandiHaler | SABA - rescue medicine |
| Terbutaline | (RS)-5-[2-(tert-butylamino)-1-hydroxyethyl]benzene-1,3-diol | Brethine, Bricanyl, Brethaire, Terbulin | SABA - rescue medicine |
| Cromolyn Sodium | disodium 5,5'-[(2-hydroxytrimethylene)dioxy]bis[4-oxo-4H-1-benzopyran-2-carboxylate] | Intal, Intal Metered Dose Inhaler | Non-steroid anti-inflammatory |
| Theophylline | 1H-Purine-2,6-dione,3,7-dihydro,1,3-dimethyl- | Uniphyl, Elixophyllin, Theo-24, Theo-Time, Theochron | Non-steroid anti-inflammatory |
| Montelukast | (S,E)-2-(1-((1-(3-(2-(7-chloroquinolin-2-yl)vinyl)phenyl)-3-(2-(2-hydroxypropan-2-yl)phenyl)propylthio)methyl)cyclopropyl)acetic acid | Singular, Montelo-10 | Leukotriene receptor antagonist (LTRA) |
| Zafirlukast | cyclopentyl 3-{2-methoxy-4-[(o-tolylsulfonyl)carbamoyl]benzyl}-1-methyl-1H-indol-5-ylcarbamate | Accolate, Accoleit, Vanticon | Leukotriene receptor antagonist (LTRA) |
| Zileuton | N-[1-(1-benzothien-2-yl)ethyl]-N-hydroxyurea | Zyflo, Zyflo CR | Leukotriene receptor antagonist (LTRA) |
| Omalizumab | Accession Number DB00043 | Xolair | Humanized Antibody |
| Dyphylline | 7-(2,3-dihydroxypropyl)-theophylline | Lufyllin | Broncodilator |
| Dyphylline in combination with Guaifenesin | 7-(2,3-dihydroxypropyl)-theophylline [and] (RS)-3-(2-methoxyphenoxy)propane-1,2-diol | COPD; Lufyllin-GG | Broncodilator and expectorant |

EXAMPLES

Example 1

Since omalizumab was approved in 2003, biologic therapies for asthma have skyrocketed, with more than 30 drugs in clinical trials and many more in development. The goal is to tailor asthma biologic therapies to specific asthma phenotypes. Given the recent approval of anti-IL5 therapies (e.g., mepolizumab and reslizumab), it is clear that identifying underlying endotypes and clinical phenotypes is essential to assign appropriate therapy.

Methods

For Urine Free BrTyr 200 ul urine was aliquoted into a glass tube with 20 ul 0.5 uM [$^{13}C_6$]—BrTyr and 1 mM [$^{13}C_9$, $^{15}N_1$]-tyrosine added as internal standard. The urine sample was diluted with 2 ml 0.1% formic acid in water and loaded to DSC-18 3 mL SPE column, previously balanced with 2×3 ml methanol and then 2×3 ml 0.1% formic acid in water. The column was washed with 2×3 ml 0.1% formic acid in water, then eluated with 2×3 ml 0.1% formic acid in 30% methanol. The elute was dried under SpeedVacuum and re-suspended in 100 ul H2O. Supernatants (5 µl) were analyzed by injection onto a Titan™ C18 UHPLC Column (1.9 µm particle size, L×I.D. 10 cm×2.1 mm, Supelco) at a flow rate of 0.4 ml min$^{-1}$ using a 2 Shimadazu LC-20AD Nexera CL pump system, SIL-30AC MP CL autosampler interfaced with an Shimadzu 8050 mass spectrometer. A discontinuous gradient was generated to resolve the analytes by mixing solvent A (0.2% formic acid in water) with solvent B (0.2% formic acid in methanol) at different ratios starting from 0% B for 3 minutes, then linearly to 100% B over 3.5 min, then hold for 3 min, and then back to 0% B. [$^{13}C_9$, $^{15}N_1$]-tyrosine was included to simultaneously monitor for potential artificial generation of analyte. 3-bromotyrosine, tyrosine and their respective internal standard [$^{13}C_6$]-3-bromotyrosine and [$^{13}C_9$, $^{15}N_1$]-tyrosine and the artificial product, [$^{13}C_9$, $^{15}N_1$]-bromotyrosine were monitored using electrospray ionization in positive-ion mode with multiple reaction monitoring (MRM) of precursor and characteristic product-ion transitions of m/z 260→135, 182→136, 266→141, 192→145 and 270→144, amu, respectively. The parameters for the ion monitoring were optimized automatically. Nitrogen (99.95% purity) was used as the source and helium was used as collision gas. Various concentrations of nonisotopically labeled 3-bromotyrosine and tyrosine standard were spiked into control urine to prepare the calibration curves for quantification of 3-bromotyrosine and tyrosine, respectively.

The internal standard [$^{13}C_6$]-3-bromotyrosine was used for quantification as well as to calculate recovery rate of 3-bromotyrosine (which was >80% based on separate control studies). Under the conditions employed for the assay, no artificial bromination was detected. Results were expressed as urine 3-bromotyrosine (ng/mg creatinine).

For Free BrTyr+Glucuronidated BrTyr 200 ul urine was aliquoted into a glass tube with 20 ul 0.5 uM [$^{13}C_6$]—BrTyr and 1 mM [$^{13}C_9$, $^{15}N_1$]-tyrosine added as internal standard. 100 ul 1 M ammonium acetate buffer, pH 5.0, was added to the urine sample followed by addition of 10 ul 16 mg/ml glucuronidase (G0751, Sigma) in water. The sample was kept at 45 C for 15 hours and then cooled down. The urine was diluted with 2 ml 0.1% formic acid in water and follow the same procedure as above for free BrTyr.

3-Bromotyroine Detection in Patients

Figure 1:
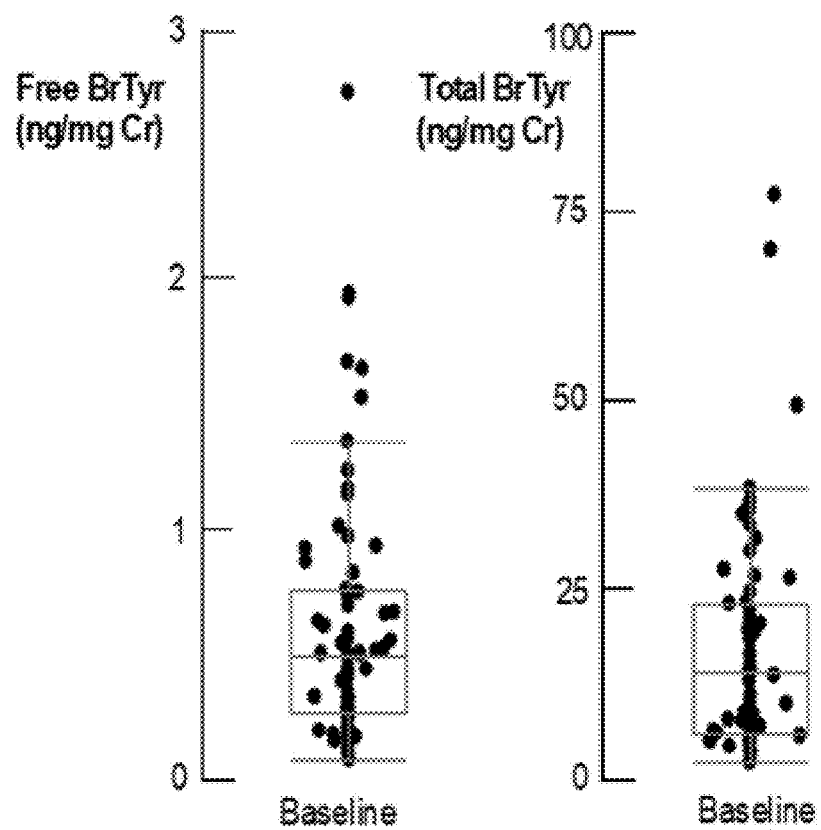
FIG. 1. The baseline distribution of Free and total BrTyr. The Box plot represent the median and interquartile range. Whiskers represent the 1st quartile−1.5*(interquartile range) and 3rd quartile+1.5*(interquartile range). Note that free (non-glucurinidated) BrTyr represents only a small fraction of the total BrTyr (~5%). Moreover, there is large variation in how much glucurinidated BrTyr there is.

BrTyr tackles this unmet clinical need. BrTyr was measured at baseline (BL), and after 3 months of injections in 68 individuals with severe asthma. There is a wide range of BrTyr levels in asthmatics as at baseline (FIG. 1, Table 1). Free BrY is the naturally free bromotyrosine in a sample, and Total BrY is the total Free Bry+4-O-glucuronide-3-bromotyrosine. Total BrY is measured in this example by de-glurcuroniting the 4-O-glucuronide-3-bromotyrosine in a sample and then measuring the level of BrY present in the sample).

TABLE 1

Baseline measurements of BrTyr

| | Baseline (n = 68) |
|---|---|
| Free BrY (ng/mg Cr) | |
| Median [25/75%] | 0.487 [0.268-0.749] |
| Mean [SE] | 0.610 [0.062] |
| Range [0%-100%] | 0.074-2.729 |
| Total BrY (ng/mg Cr) | |
| Median [25/75%] | 13.64 [6.00-22.72] |
| Mean [SE] | 16.92 [1.78] |
| Range [0%-100%] | 1.94-77.16 |
| % Free BrY [(Free/total)*100] | |
| Median [25/75%] | 3.68 [1.71-7.35] |
| Mean [SE] | 5.64 [0.7] |
| Range [0%-100%] | 0.87-33.07 |

Figure 2:
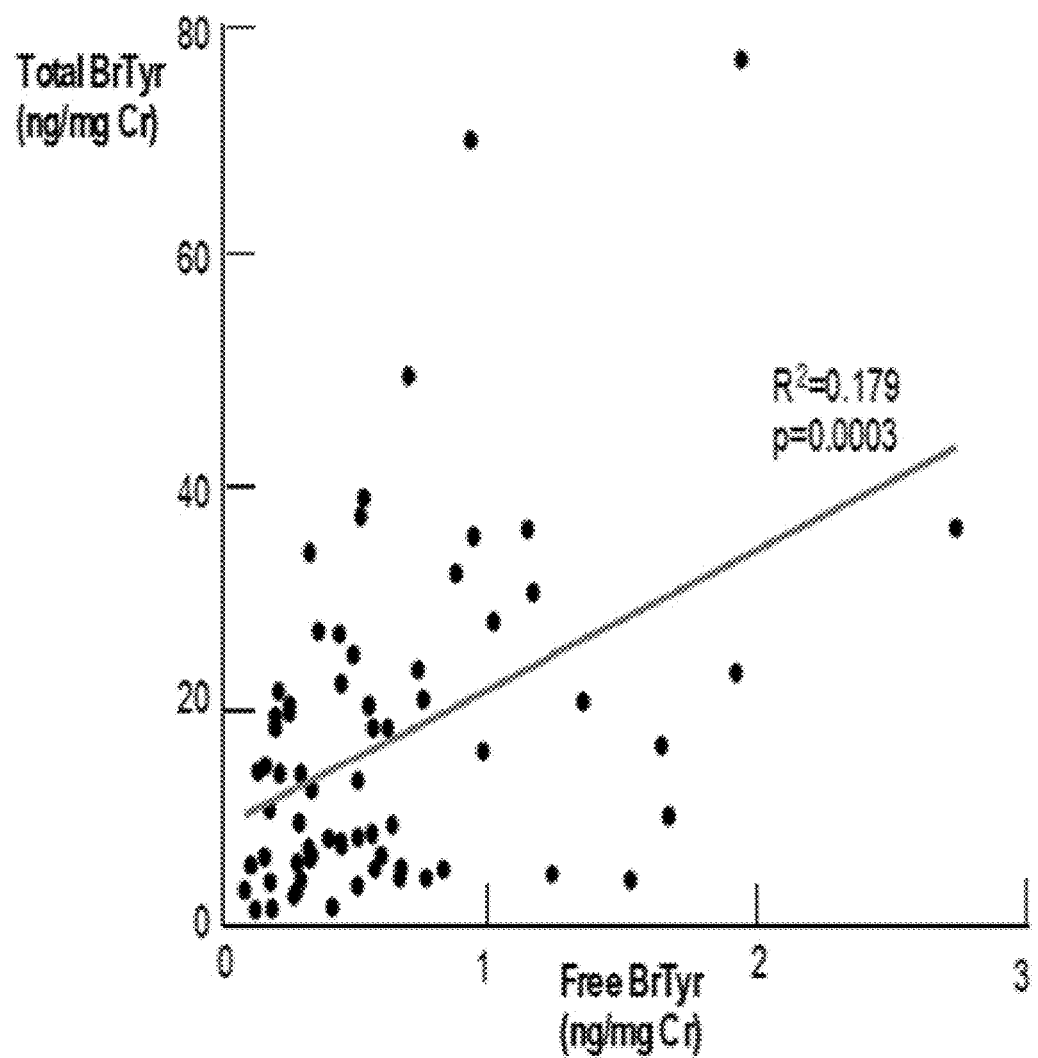
FIG. 2. Correlation between Free and "Total" BrTyr. Total BrTyr is generated by glucuronidase enzyme digestion treatment. Only 17.9% of variation in free BrTyr levels are accounted for by variations in Total BrTyr. Thus, while there exists a modest statistical correlation, the two measures are fundamentally independent of one another.

Most of the BrTyr present in the total BrTyr is 4-O-glucurinided-3 bromotyrosine (% free BrTyr, median (IQR): 3.68 (1.71-7.35); Table 1). FIG. 2 demonstrates the correlation between baseline Total BrTyr and naturally Free BrTyr ($R2=0.179$, $P=0.0003$).

All patients had uniform drop in eosinophils by 3 months (Bsln eosinophil numbers 440±77 vs. 3 months after mepolizumab 62±0.8; P<0.001), but overall BrTyr (free and total) levels did not significantly change among individuals with some dropping and others not (BrTyr (ng/mg Cr), mean±SE: Bsln Free BrTyr 0.610±0.0620 vs 3 months after mepolizumab 0.782±0.117, p=0.11; Bsln Total BrTyr 16.92±1.78 vs 3 months after mepolizumab 18.08±1.85, p=0.51).

In this phenotype designated as Th2-high (by blood eosinophil counts), there existed a BrTyr subgroup of patients (45% of asthmatics have an decrease in BrTyr after mepolizumab) with activated eosinophils that were the most likely to respond to mepolizumab. These data also indicate that one in four asthmatics who have eosinophil counts>150, may have greater benefit from therapies targeting non-eosinophilic pathways (that are less expensive).

Figure 3:
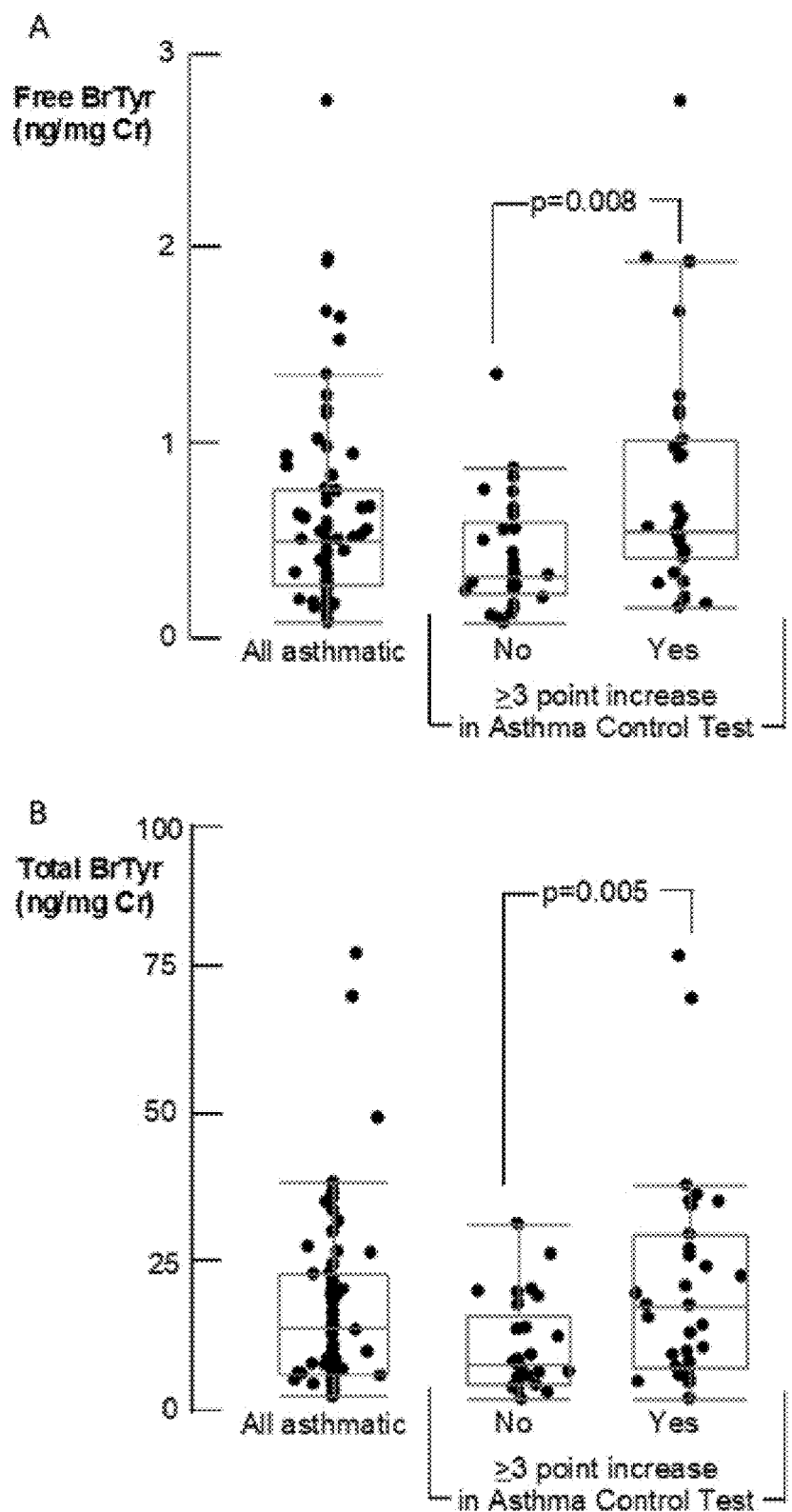
FIG. 3. Free (Panel A) and Total (Panel B) BrTyr baseline levels of asthmatics that increase their asthma control test with 3 or more points after 3 months of mepolizumab. Asthmatics that show improvement in quantitative assessments of symptoms (increase of their asthma control test by 3 or more points) following 3 months of mepolizumab therapy have higher levels of both Free (Panel A) and Total (Panel B) BrTyr at baseline. Those with the highest BrTyr levels, evidence of eosinophil activation and tissue injury, are most likely to show improvement in Asthma Control Test results (reduction in symptom severity on drug).

The Asthma control test (ACT) is a numerical score to measure if asthma symptoms are well controlled. An increase of 3 points or more is considered likely evidence to indicate a clinically meaningful change in asthma control in an individual patient over time. More than 50% (53%) of the asthmatics showed an increase of 3 points or more in their ACT score after 3 months of mepolizumab. This also means that nearly half of the subjects on this highly expensive biologic agent failed to show benefit. Therefore, having a biomarker that can identify those who are more likely to benefit, and those less likely to benefit, is an important advance. The baseline BrTyr levels of Free as well as Total BrTyr, were significantly higher in the groups of asthmatics that showed a significant clinically relevant improvement (> or =3 point increase) in their asthma control test (FIG. 3).

BrTyr as Predictor of Clinical Response to Mepolizumab

Figure 5B:
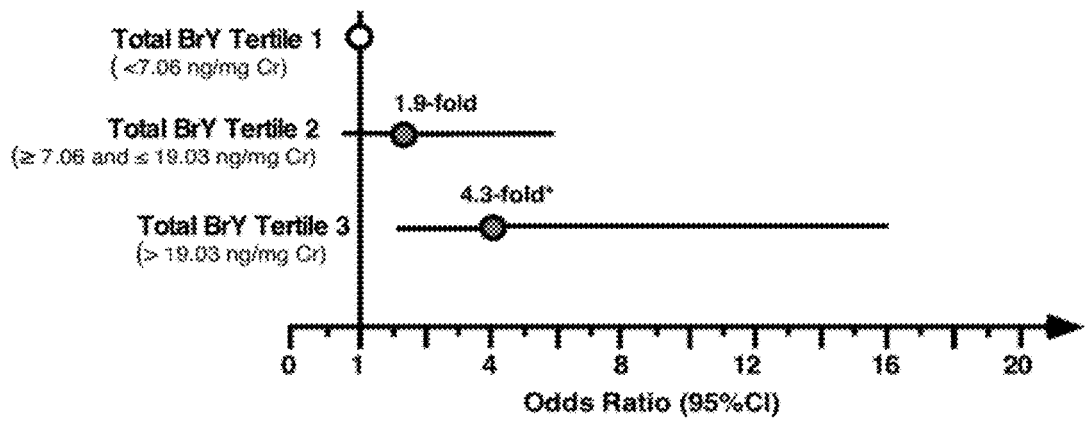
Figure 5D:
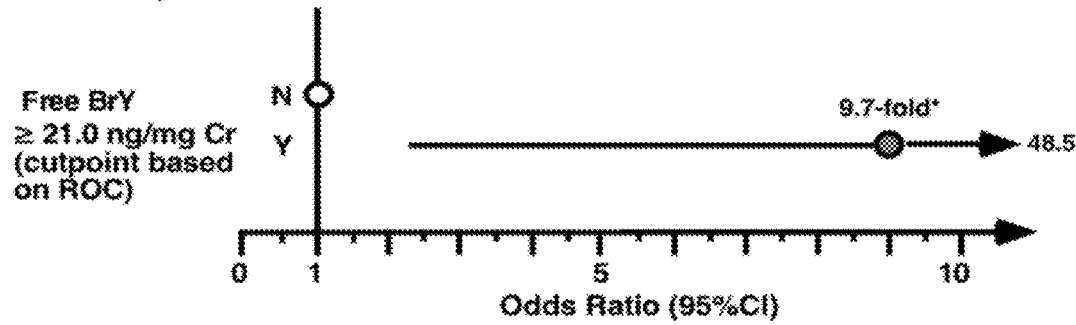

Median, Tertiles, Quartiles and Receiver operating characteristic curve analyses were used to assess the utility of BrTyr measurements at baseline for the prediction of clinical responsiveness to mepolizumab. The clinical responsiveness in this Example was defined as an improvement of 3 or more point in their asthma control test after 3 months of mepolizumab. FIGS. 4 and 5 shows the ODD ratios for Free and total BrTyr as a predictor for mepolizumab response based on the asthma control test. Those with higher baseline BrTyr levels (both free and total) have increased likelihood of improvement in asthma questionnaire. Total BrTyr levels (measured after urine incubation with the glucuronidase enzyme digestion treatment) are 10-20 fold higher, and easier to measure, and show improved accuracy as well.

There is a wide range of changes in BrTyr levels after 3 months of mepolizumab, as shown in Table 2.

TABLE 2

The distribution of the delta free and Total BrTyr (3 months mepolizumab minus Baseline)

| | (n = 68) |
|---|---|
| Delta Free BrY (ng/mg Cr) | |
| Median [25/75%] | 0.028 [−0.195-2.89] |
| Mean [SE] | 0.172 [0.122] |
| Range [0-100%] | −1.67-4.65 |
| Total BrY (ng/mg Cr) | |
| Median [25/75%] | 0.979 [−4.85-5.27] |
| Mean [SE] | 1.165 [1.77] |
| Range [0-100%] | −55.0-46.6 |

Both free and total BrTyr levels show large variation before vs 3 months following initiation of mepolizumab therapy. While not shown in Table 2, patients also show large variation in response to therapy (e.g., a large fraction fail to show benefit). This raised the possibility that those which showed the highest initial levels of eosinoiphilic tissue injury at baseline (highest free and/or Total Br Tyr level) or largest reduction in BrTyr level, are most likely to show benefit with therapy. The change in free and total BrTyr (BrTyr levels at 3 months mepolizumab minus baseline measurement of BrTyr) is not associated with the change in asthma control test.

Steroids Decrease BrTyr

Figure 6:
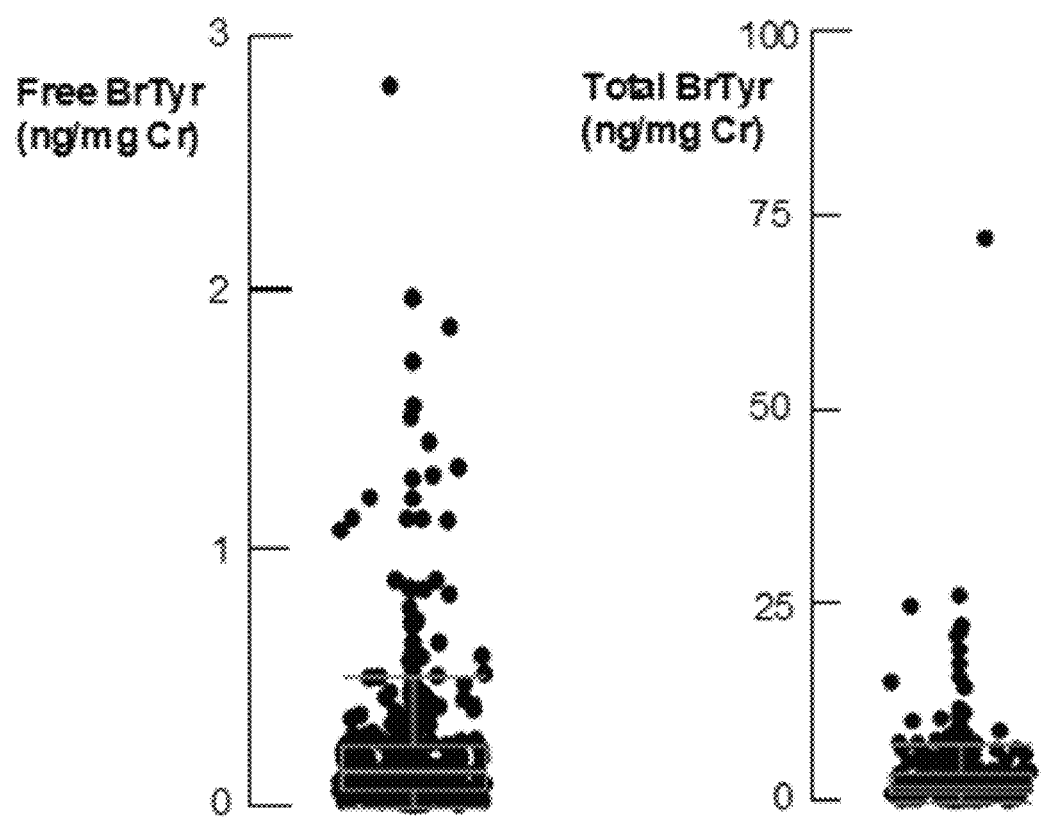
FIG. 6. The baseline distribution of Free and total BrTyr. The Box plot represent the median and the 75 and 25 percentile cutoffs. The whiskers represent the 1st quartile−1.5*(interquartile range) and 3rd quartile+1.5*(interquartile range).

As a site in the ongoing longitudinal NHLBI SARP3, we are evaluating asthmatics (severe and non-severe) that are stable on their current medications at baseline enrollment and then 2-3 weeks after intramuscular triamcinolone injection. BrTyr was measured at baseline (BL), and 2-3 weeks after intramuscular triamcinolone injection in 464 adults with asthma. There is a wide range of BrTyr levels in asthmatics at baseline (FIG. 6, Table 3). Most of the BrTyr present in the total measurement of BrTyr is present as 4-O-glucurinided-3 bromotyrosine (Table 3).

TABLE 3

Baseline and 2-3 weeks after intramuscular triamcinolone injection measurements of BrTyr in Severe Asthma Research Cohort

|  | Baseline (n = 464) | After 2-3 wks of intramuscular triamcinolone injection (n = 464) |
|---|---|---|
| Free BrY (ng/mg Cr) | | |
| Median [25/75%] | 0.139 [0.063-0.25] | 0.112 [0.061-0.224] |
| Mean [SE] | 0.241 [0.017] | 0.208 [0.015] |
| Range {0-100%} | 0.003-4.149 | 0.002-3.720 |
| Total BrY (ng/mg Cr) | | 1.93 [1.01-3.43]* |
| Median [25/75%] | 2.28 [1.27-4.01] | 2.93 [0.17] |
| Mean [SE] | 3.50 [0.23] | 0.11-46.4 |
| Range {0-100%} | 0.23-74 | |
| % Free BrY [(Free/total)*100] | 5.89 [2.41-13.86] | 6.96 [2.88-13.94] |
| Median [25/75%] | 10.91 [0.62 | 11.51 [0.62] |
| Mean [SE] | 0.04 89.6 | 0.18-88.1] |
| Range [0%-100%] | | |

FIG. 6 demonstrate the correlation between baseline Total BrTyr and Free BrTyr (R2=0.029, P=0.0002), showing minimal association (measurement of total BrTyr only explains 2.9% of the variation in free BrTyr). Interestingly, Total BrTyr decreases significantly after intramuscular triamcinolone injection (p=0.018) whereas no significant change is found with Free BrTyr (p=0.08).

In summary, the above work asked whether free or Total BrTyr predicts likelihood of exacerbation during a steroid withdraw study in mild asthmatics. Subjects were given an intramuscular injection of steroid, and then the frequency of worsening of asthma symptoms monitored over time during the steroid withdraw period. Again note that Total BrTyr is nearly 50-fold higher than free BrTyr, indicating the vast majority of BrTyr is glucuroinidated and not monitored when quantifying free BrTyr in urine without the glucuronidase enzyme digestion step. Also note in FIG. 7 that Free vs Total BrTyr are poorly correlated. Only 2.9% of the variation in Free BrTyr levels is explained by variations in Total BrTyr levels (they are essentially independent values).

Figure 7:
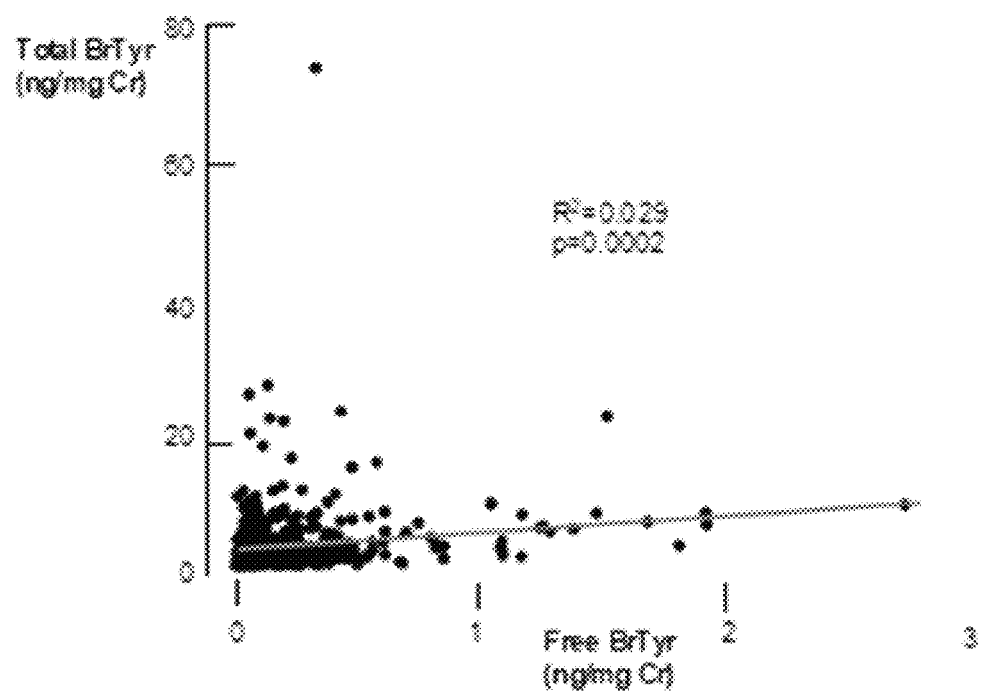
FIG. 7. The correlation between Free and total BrTyr in the severe asthma cohort at baseline (before steroid withdraw).

Asthmatics with unscheduled doctor (MD) visits and emergency room (ER) visits in the last 12 months had significantly higher total BrTyr levels at baseline whereas no difference was found with Free BrTyr (Table 4, FIG. 7).

TABLE 4

Comparison of asthma phenotypes and Baseline measurements of BrTyr in Severe Asthma Research Cohort

| Phenotype (N) | Free BrTyr | Total Brtyr |
|---|---|---|
| SARP3 Nonsevere (204) | 0.23 (0.03) | 3.27 (0.23) |
| SARP3 Severe (317) | 0.25 (0.38) | 3.71 (0.33) |
| P | 0.5 | 0.3 |
| No unscheduled MD visits last year (276) | 0.23 (0.02) | 3.13 (0.21) |
| Yes, Unscheduled MD visits last year (213) | 0.26 (0.03) | 4.05 (0.43) |
| P | 0.4 | 0.0141 |
| No ED visits (373) | 0.24 (0.02) | 3.26 (0.18) |
| Yes, ED visit last year (116) | 0.25 (0.04) | 4.43 (0.72) |
| P | 0.7 | 0.042 |

Data are represented as mean and SD. P-values are based on nonparametric t-test

It is clear that total BrTyr levels predict likelihood of unscheduled MD visit or ED visit.

Figure 8:
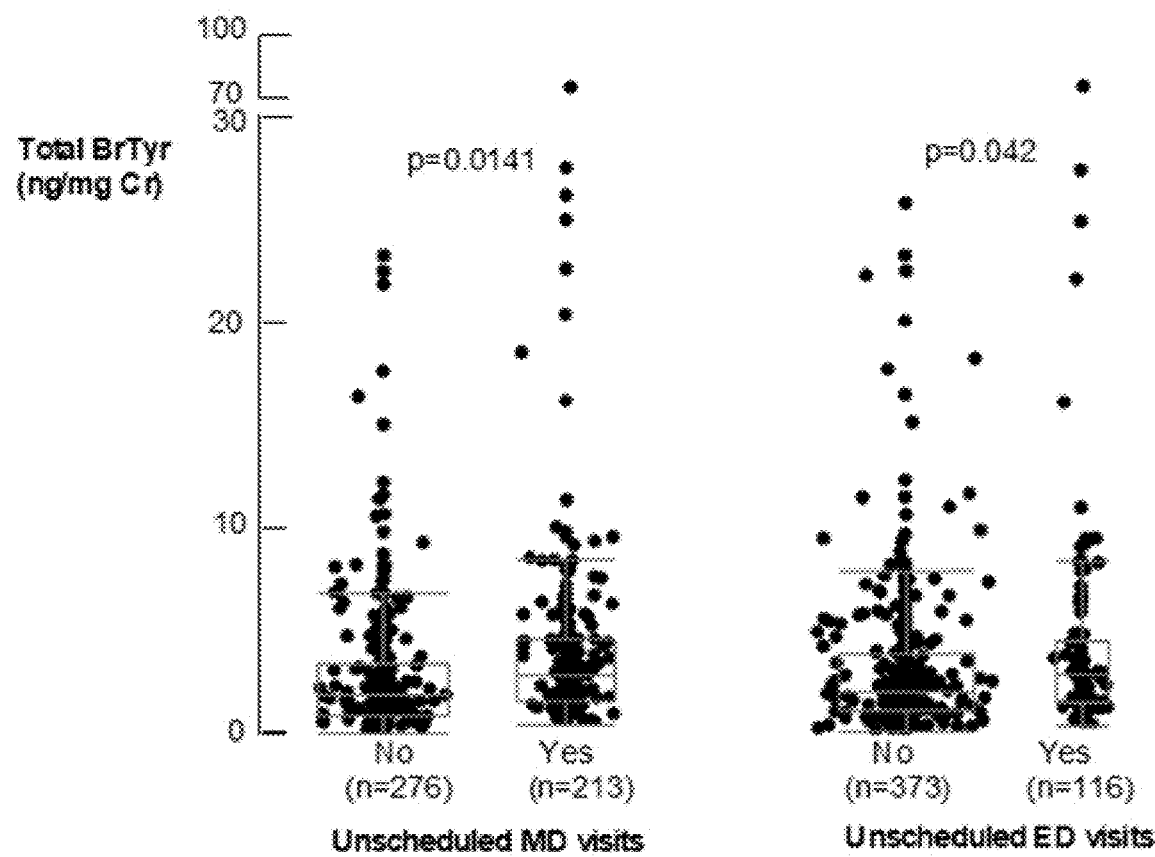
FIG. 8. Baseline Total BrTyr levels in asthma phenotypes.
Figure 9:
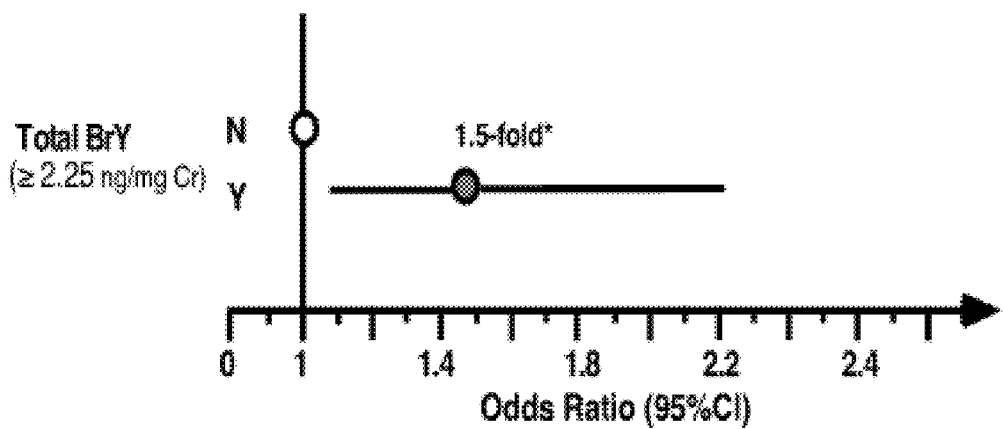
FIG. 9. ORs and 95% CI for the associations between Total BrTyr levels and unscheduled MD visits. Results shown represent the ORs (circles) and 95% CI (lines) of unscheduled MD visited and (A) high level of bromotyrosine (greater than median level of 2.25 ng/mg cr, filled circle) versus not a high level (open circle) and (B) high level of bromotyrosine (greater than <1.60 ng/mg Cr), filled circle) versus not a high level (open circle).
Figure 9:
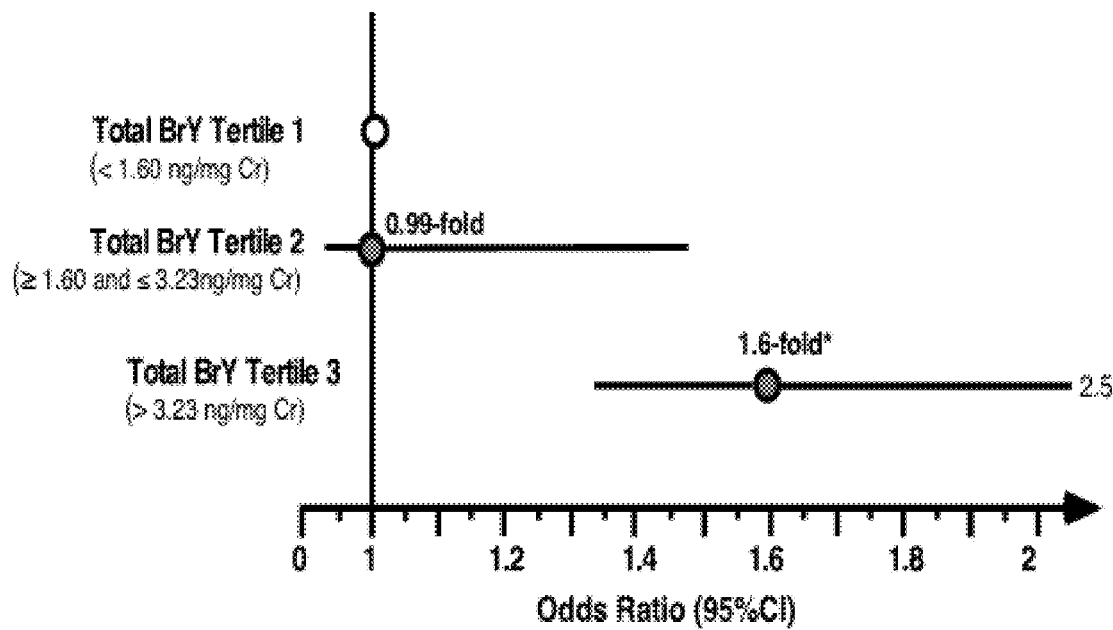

Median and Tertiles were used to assess the utility of BrTyr measurements at baseline for the prediction of asthma control based on unscheduled doctor visits. High levels of Total BrTyr predict an increased risk for unscheduled doctor visits, whereas no correlation was found with free BrTyr. (FIG. 8) FIG. 9 shows ORs and 95% CI for the associations between Total BrTyr levels and unscheduled MD visits. Results shown represent the ORs (circles) and 95% CI (lines) of unscheduled MD visited and (A) high level of bromotyrosine (greater than median level of 2.25 ng/mg cr, filled circle) versus not a high level (open circle) and (B) high level of bromotyrosine (greater than <1.60 ng/mg Cr), filled circle) versus not a high level (open circle). Subjects with higher level of urinary total BrTyr were more likely to experience unscheduled MD visits. When Total urinary BrTyr is measured, whether one stratifies above v below median value, or by tertile levels, one sees higher levels of BrTyr predict worse outcome, and more unscheduled MD visits for worsening asthma symptoms. Thus, Total BrTyr dose dependently predicts worse outcome.

REFERENCES

1. J. Pediatrics, 2011, 159, 248-255—Samuel H. Wedges et. al.
2. Clin. Trans. Science, 2, 2009, 112-117—Samuel H Wedges et. al
3. J. Allergy Clin Immunol, 2015, 135 (4) 877-883—Douglas C. Cowan et. al.
4. U.S. Pat. No. 6,306,576—Diagnostic methods for asthma All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
   a) a urine sample from a subject having, or suspected of having, asthma and/or an eosinophilic disorder; and
   b) a de-glucuronidation agent that, when added to said urine sample to generate a composition, liberates 3-bromotyrosine from 4-O-glucuronide-3-bromotyrosine in said urine sample to generate free bromotyrosine, and
   c) stable isotope labeled 3-bromotyrosine molecules.

2. The system of claim 1, wherein said de-glucuronidation agent comprises β-glucuronidase.

3. The system of claim 1, wherein said urine sample is from a subject with asthma.

4. The system of claim 1, wherein said urine sample is from a subject suspected of having asthma.

5. A composition comprising:
   a) a urine sample from a subject having, or suspected of having, asthma and/or an eosinophilic disorder;
   b) a de-glucuronidation agent that has liberated 3-bromotyrosine from 4-O-glucuronide-3-bromotyrosine in said urine sample; and
   c) stable isotope labeled 3-bromotyrosine molecules.

6. The composition of claim 5, wherein said de-glucuronidation agent comprises β-glucuronidase.

7. The composition of claim 5, wherein said de-glucuronidation agent comprises a base.

8. The composition of claim 5, wherein said de-glucuronidation agent comprises an acid.

* * * * *